(12) United States Patent
Park et al.

(10) Patent No.: US 9,947,873 B2
(45) Date of Patent: Apr. 17, 2018

(54) FUSED POLYCYCLIC HETEROAROMATIC COMPOUND, ORGANIC THIN FILM INCLUDING COMPOUND AND ELECTRONIC DEVICE INCLUDING ORGANIC THIN FILM

(71) Applicant: Samsung Electronics Co., Ltd., Suwon-si, Gyeonggi-do (KR)

(72) Inventors: Jeong Il Park, Seongnam-si (KR); Hyun Bum Kang, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/621,021

(22) Filed: Jun. 13, 2017

(65) Prior Publication Data

US 2017/0358752 A1    Dec. 14, 2017

(30) Foreign Application Priority Data

Jun. 13, 2016    (KR) ........................ 10-2016-0073004

(51) Int. Cl.
| | |
|---|---|
| *C07D 487/22* | (2006.01) |
| *C07D 495/22* | (2006.01) |
| *C07D 513/22* | (2006.01) |
| *C07D 517/22* | (2006.01) |
| *H01L 51/00* | (2006.01) |
| *H01L 51/05* | (2006.01) |

(52) U.S. Cl.
CPC ........ *H01L 51/0056* (2013.01); *C07D 487/22* (2013.01); *C07D 495/22* (2013.01); *C07D 513/22* (2013.01); *C07D 517/22* (2013.01); *H01L 51/0062* (2013.01); *H01L 51/0508* (2013.01)

(58) Field of Classification Search
CPC .. C07D 487/22; C07D 495/22; C07D 513/22; C07D 517/22; H01L 51/0056; H01L 51/0062; H01L 51/0508
See application file for complete search history.

(56) References Cited

U.S. PATENT DOCUMENTS

| | | | |
|---|---|---|---|
| 7,816,673 | B2 | 10/2010 | Park et al. |
| 9,175,212 | B2 | 11/2015 | Zuberi et al. |
| 2012/0012827 | A1* | 1/2012 | Horiuchi ............... C09K 11/06 257/40 |
| 2015/0144847 | A1 | 5/2015 | D'Lavari et al. |

FOREIGN PATENT DOCUMENTS

| | | |
|---|---|---|
| JP | 2006290192 A | 10/2006 |
| KR | 2011-0102377 A | 9/2011 |
| KR | 2015-0016255 A | 2/2015 |
| WO | WO-2009/009790 A1 | 1/2009 |

OTHER PUBLICATIONS

Solution-pinted organic semiconductor blends exhibiting transport properties on par with single crystals, Muhammad R. Niazi et al., Nature Communications, 6, 8598, Nov. 23, 2015.

* cited by examiner

*Primary Examiner* — Timothy R Rozof
(74) *Attorney, Agent, or Firm* — Harness, Dickey & Pierce, P.L.C.

(57) ABSTRACT

A low-molecular-weight fused polycyclic heteroaromatic compound has a compact planar structure in which seven or more aromatic rings and heteroaromatic rings are fused together, and thereby exhibits relatively high charge mobility, and improved processability due to improved dissolubility for a solvent. An organic thin film and an electronic device include the fused polycyclic heteroaromatic compound expressed in Chemical Formula 1.

13 Claims, 2 Drawing Sheets

FUSED POLYCYCLIC HETEROAROMATIC COMPOUND, ORGANIC THIN FILM INCLUDING COMPOUND AND ELECTRONIC DEVICE INCLUDING ORGANIC THIN FILM

CROSS-REFERENCE TO RELATED APPLICATION

This application claims priority to Korean Patent Application No. 10-2016-0073004, filed in the Korean Intellectual Property Office on Jun. 13, 2016, and all the benefits accruing therefrom under 35 U.S.C. § 119, the entire contents of which are incorporated herein by reference.

BACKGROUND

1. Field

Example embodiments relate to a fused polycyclic heteroaromatic compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to the operation of the gate electrode. The semiconductor layer may include an organic semiconductor material that is controlled by a current between the source electrode and the drain electrode using an applied gate voltage.

Recently, as an organic semiconductor material for a channel of the thin film transistor, low-molecular-weight organic materials, e.g., pentacene or a polymer organic material (e.g., polythiophene), have been studied.

However, the polymer organic materials have relatively low charge mobility and relatively high off-state leakage current. Further, relatively low-molecular-weight organic materials, e.g., pentacene, may have a relatively high charge mobility of about 3.2 $cm^2/Vs$ to about 5.0 $cm^2/Vs$ or more, but may require a relatively expensive apparatus for vacuum deposition at the time of forming a thin film. Therefore, the low-molecular-weight organic material may be unsuitable for use in the preparation of a film having a relatively large area, and processibility may be undesirable.

SUMMARY

In view of the above, the development of an organic semiconductor material having improved electrical properties and processibility, may be advantageous.

Some example embodiments provide a relatively low-molecular-weight fused polycyclic heteroaromatic compound that has a compact planar structure in which seven or more aromatic rings and heteroaromatic rings are fused together, and thereby exhibits relatively high charge mobility, and furthermore has improved processibility, due to improved dissolubility for a solvent.

Some example embodiments also provide an organic thin film including the fused polycyclic heteroaromatic compound.

Some example embodiments also provide an electronic device including the organic thin film.

According to some example embodiments, a fused polycyclic heteroaromatic compound is represented by Chemical Formula 1.

[Chemical Formula 1]

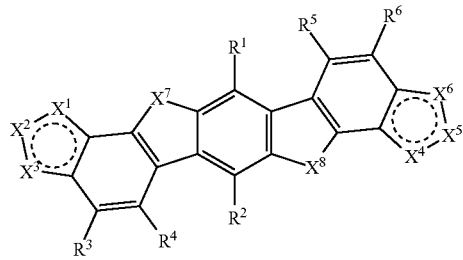

In Chemical Formula 1, $X^1$ to $X^8$ are independently one of S, Se, Te, N—$R^a$, and C—$R^b$, wherein $R^a$ and $R^b$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, one of $X^1$ to $X^3$ is one of S, Se, Te, and N—$R^a$ and remaining two of $X^1$ to $X^3$ are C—$R^b$ wherein $R^b$ is one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group or $R^b$'s are linked with each other to provide a $C_5$ aromatic ring or a $C_6$ aromatic ring, one of $X^4$ to $X^6$ is one of S, Se, Te, and N—$R^a$ and remaining two of $X^4$ to $X^6$ are C—$R^b$ wherein $R^b$ is one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group or $R^b$'s are linked with each other to provide a $C_5$ aromatic ring or a $C_6$ aromatic ring, each of $R^3$ to $R^6$ is independently one of hydrogen, a halogen, a cyano group, a $C_1$ to $C_4$ alkyl group, and a $C_1$ to $C_4$ fluoroalkyl group, and each of $R^1$ and $R^2$ is independently a functional group represented by Chemical Formula 2,

*-L-$Y^1$            [Chemical Formula 2]

wherein, in Chemical Formula 2,

L is an ethynylene group or a functional group represented by Chemical Formula 2-1, and $Y^1$ is one of hydrogen, a halogen, a cyano group, —Si($R^x$)($R^y$)($R^z$) (wherein each of $R^x$, $R^y$, and $R^z$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group), a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group,

[Chemical Formula 2-1]

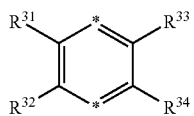

wherein, in Chemical Formula 2-1, each of $R^{31}$ to $R^{34}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group or optionally $R^{31}$ and $R^{32}$ are linked with each other to provide a $C_5$ aromatic ring or a $C_6$ aromatic ring or optionally $R^{33}$ and $R^{34}$ are linked with each other to provide a $C_5$ aromatic ring or a $C_6$ aromatic ring.

The fused polycyclic heteroaromatic compound represented by Chemical Formula 1 may be one of compounds represented by Chemical Formulae 1-1 to 1-3.

[Chemical Formula 1-1]

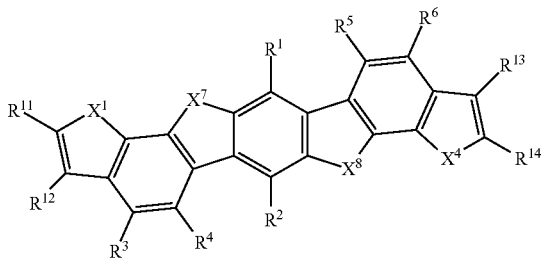

[Chemical Formula 1-2]

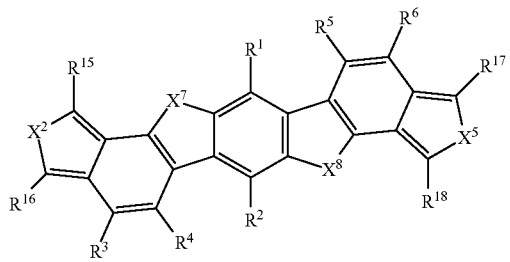

[Chemical Formula 1-3]

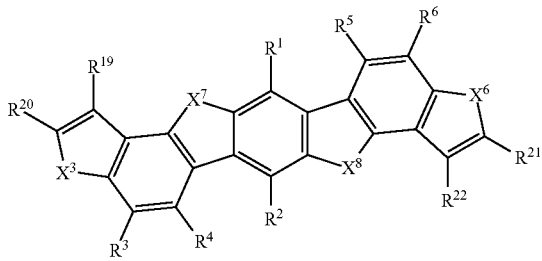

In Chemical Formulae 1-1 to 1-3, $R^1$ to $R^6$ are the same as in Chemical Formula 1, each of $X^1$ to $X^8$ is one of S, Se, Te, and N—$R^a$, wherein $R^a$ is one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, and each of $R^{11}$ to $R^{22}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, or optionally at least one of $R^{11}$ and $R^{12}$ and $R^{13}$ and $R^{14}$ or at least one of $R^{19}$ and $R^{20}$ and $R^{21}$ and $R^{22}$ are linked with each other to provide a $C_5$ aromatic ring or a $C_6$ aromatic ring.

In Chemical Formula 1, one of $X^1$ to $X^3$ may independently be a sulfur atom (S) or a selenium atom (Se) and one of $X^4$ to $X^6$ may independently be a sulfur atom (S) or a selenium atom (Se).

In Chemical Formula 1, the $C_5$ aromatic ring or the $C_6$ aromatic ring may respectively be an $X^9$-containing ring and an $X^{10}$-containing ring wherein $X^9$ and $X^{10}$ are independently one of O, S, Se, Te, N—$R^a$, and $C(R^c)$=$C(R^d)$, wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

In Chemical Formula 2, the $C_5$ aromatic ring or the $C_6$ aromatic ring may respectively be an $X^{11}$-containing ring and an $X^{12}$-containing ring, wherein $X^{11}$ and $X^{12}$ are independently one of O, S, Se, Te, N—$R^a$, and $C(R^c)$=$C(R^d)$, wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

The functional group represented by Chemical Formula 2-1 may be one of functional groups represented by Chemical Formula 2-1-1.

[Chemical Formula 2-1-1]

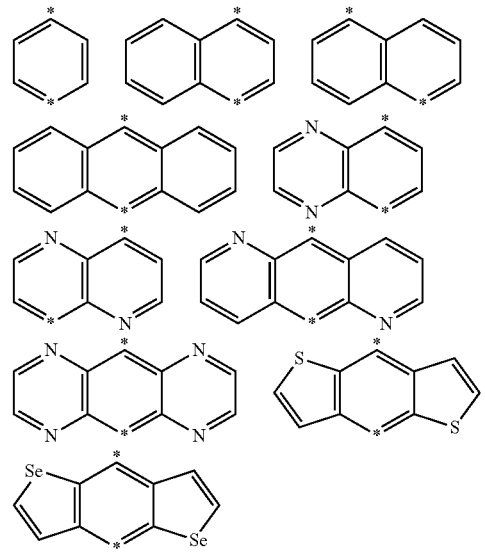

The fused polycyclic heteroaromatic compound may have a molecular weight of about 300 to about 3000.

The fused polycyclic heteroaromatic compound may be for example compounds of Chemical Formula 1-1-1, 1-2-1, or 1-3-1.
[Chemical Formula 1-1-1]
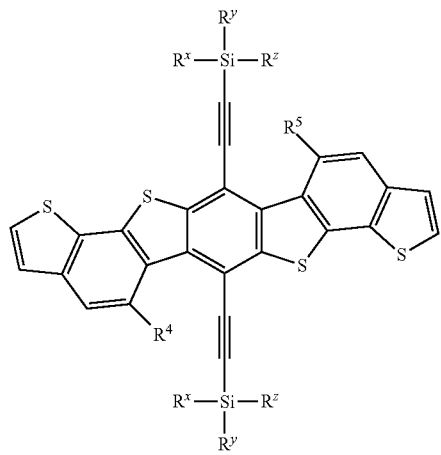
(1)
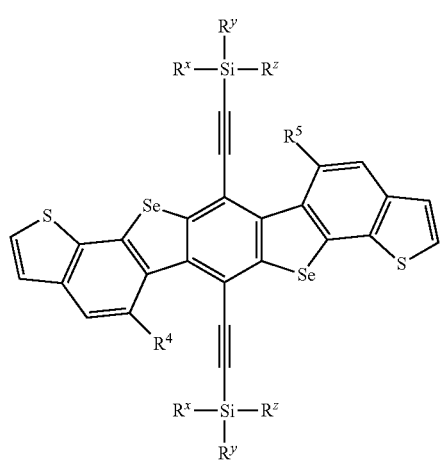
(2)
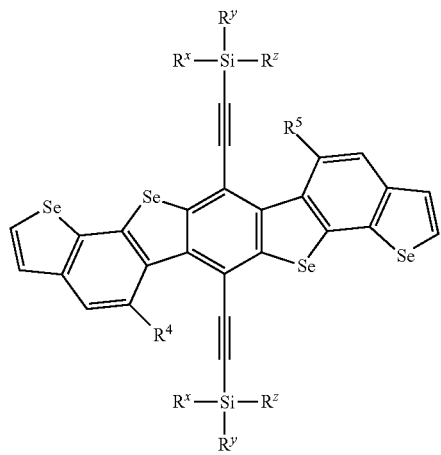
(3)
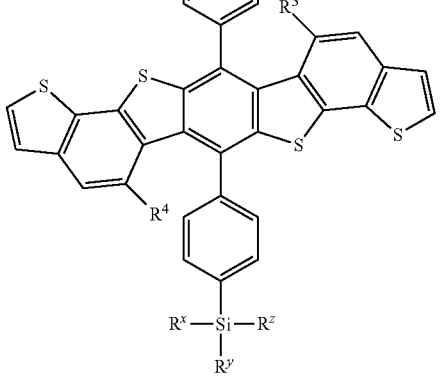
(4)
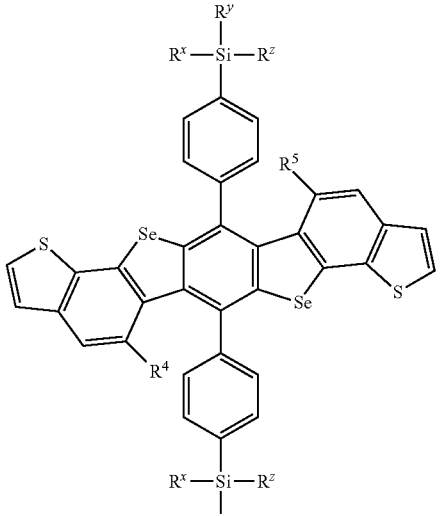
(5)
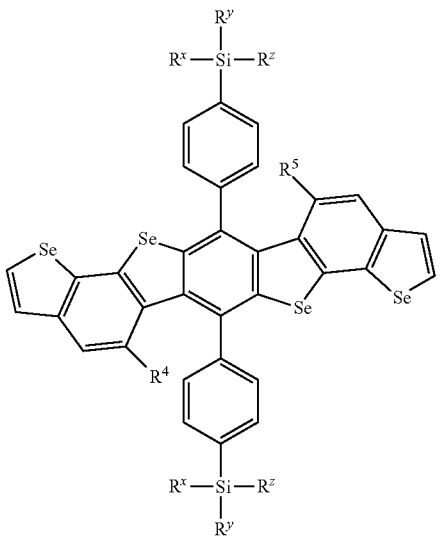
(6)

[Chemical Formula 1-2-1]
(1)
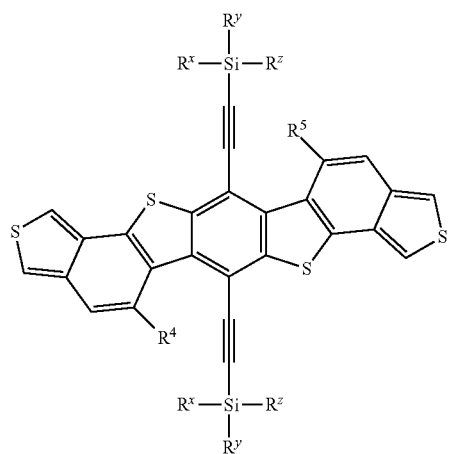
(2)
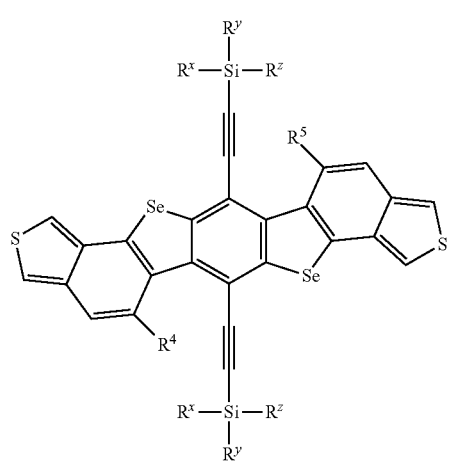
(3)
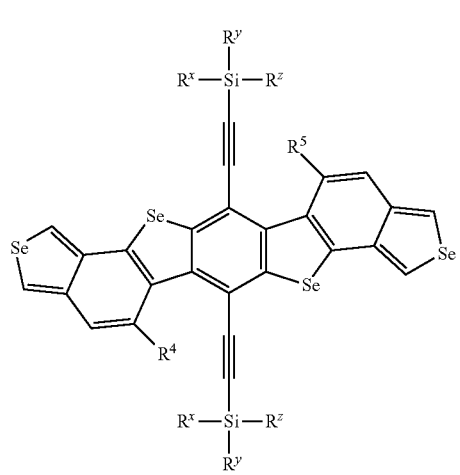
(4)
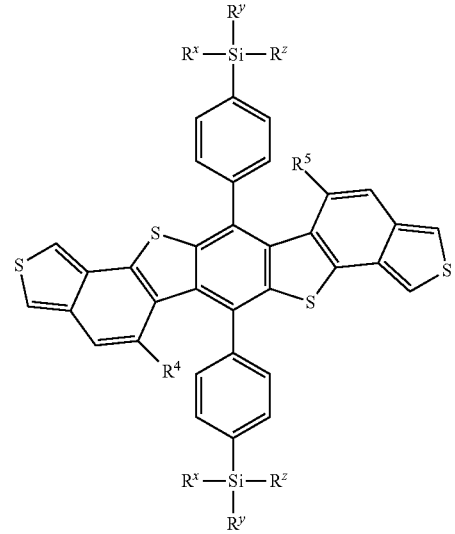
(5)
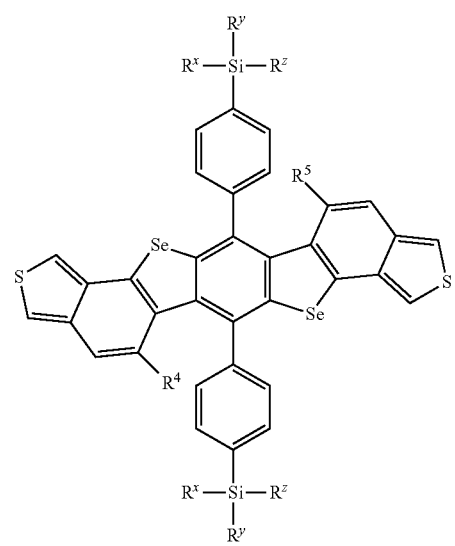
(6)
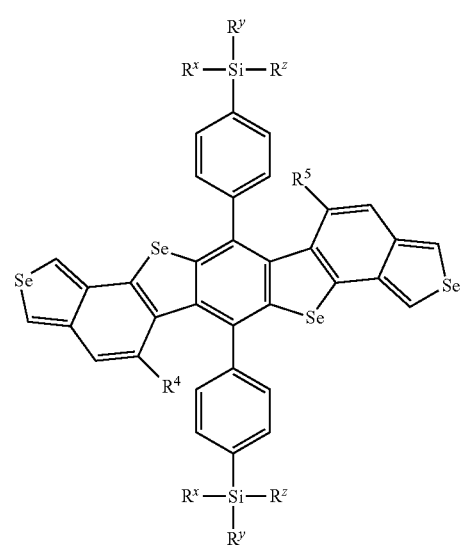

-continued
[Chemical Formula 1-3-1]
(1)
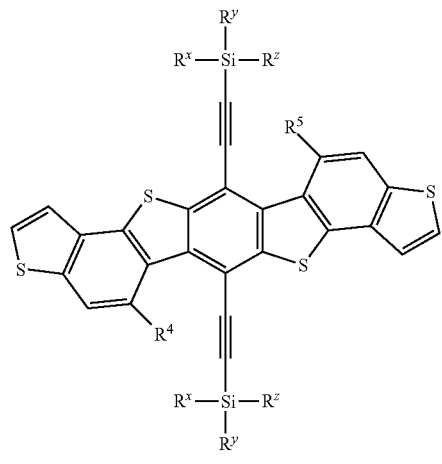
(2)
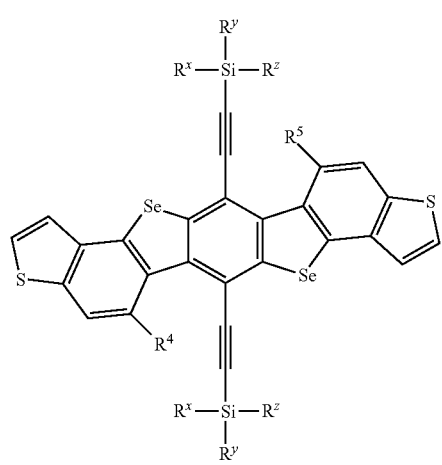
(3)
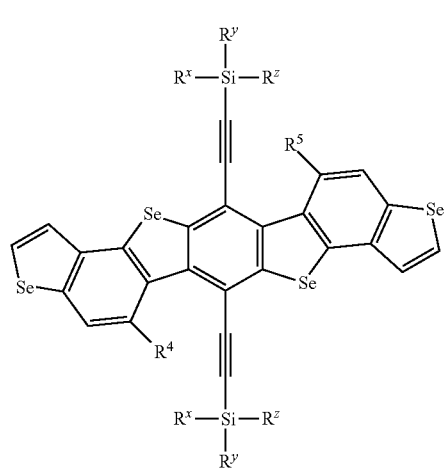
-continued
(4)
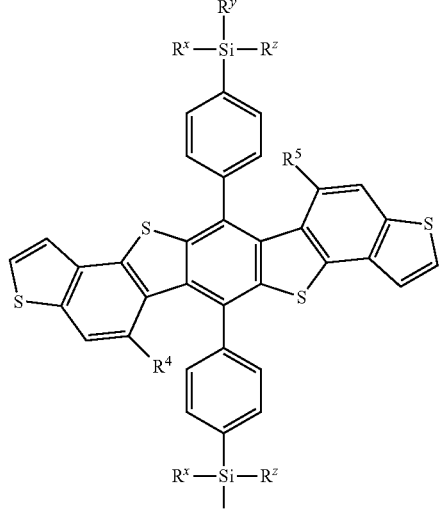
(5)
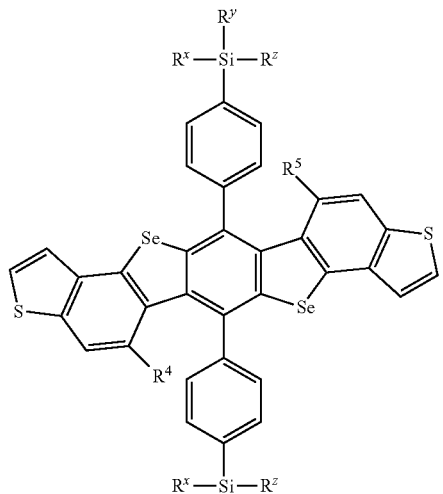
(6)
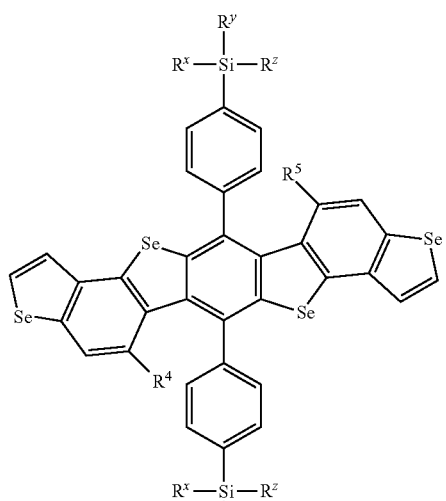
In Chemical Formulae 1-1-1, 1-2-1, and 1-3-1,
each of $R^4$ and $R^5$ is independently one of hydrogen, a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, each of $R^x$, $R^y$, $R^z$, $R'^x$, $R'^y$, and $R'^z$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, a substituted or unsubstituted $C_4$ to $C_{10}$ heteroaryl group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

According to some example embodiments, an organic thin film includes the fused polycyclic heteroaromatic compound.

According to some example embodiments, an electronic device includes the fused polycyclic heteroaromatic compound.

DETAILED DESCRIPTION

Figure 1:
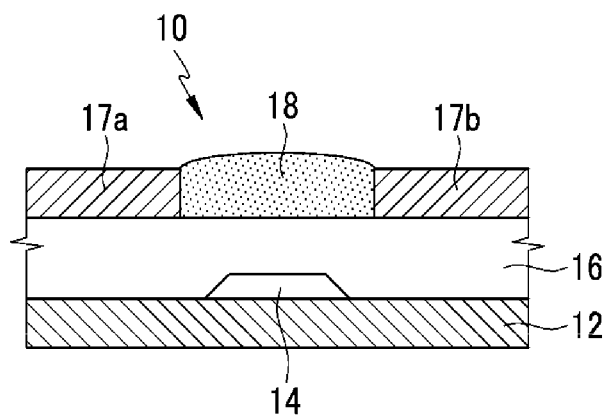
FIG. 1 is a schematic cross-sectional view of a transistor according to some example embodiments.

The example embodiments will be described more fully hereinafter with reference to the accompanying drawings, in which example embodiments are shown. However, the example embodiments may be embodied in many different forms and are not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, the term "combination thereof" refers to a mutual substituent, a mixture, a stacked structure, etc.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the example embodiments may be cylindrical, other tubular cross-sectional forms are contemplated, such as square, rectangular, oval, triangular and others.

As used herein, when a definition is not otherwise provided, the prefix "hetero" may refer to a group that includes 1 to 4 heteroatoms, each independently one of N, O, S, Se, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. Heterocycloalkyl groups include at least one non-aromatic ring that contains a heteroatom ring member. Heteroaryl groups include at least one aromatic ring that contains a heteroatom ring member. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, etc.).

As used herein, when a definition is not otherwise provided, the term "aryl group" may refer to a monovalent functional group formed by the removal of one hydrogen atom from a ring of an arene, e.g., phenyl or naphthyl. The arene may refer to a hydrocarbon having an aromatic ring, and includes monocyclic and polycyclic hydrocarbons, wherein the additional ring(s) of the polycyclic hydrocarbon may be aromatic or nonaromatic.

As used herein, when a definition is not otherwise provided, the term "arylalkyl group" may refer to the aryl group defined above where at least one hydrogen atom is substituted with a lower alkylene, e.g., methylene, ethylene, propylene, etc. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "heteroarylalkyl group" may refer to the alkyl group defined above where at least one hydrogen atom is substituted with a heteroaryl group.

The term "alkylheteroaryl group" may refer to the heteroaryl group defined above, where at least one hydrogen atom is substituted with alkyl group.

As used herein, when a definition is not otherwise provided, the term "aromatic ring" refers to a functional group in which all atoms in the cyclic functional group have a p-orbital, and wherein these p-orbitals are conjugated. For example, the aromatic ring may be a C6 to C20 aryl group.

As used herein, when a definition is not otherwise provided, the term "substituted" means that a functional group or a compound is substituted with at least one substituent independently selected from a halogen (—F, —Cl, —Br, or —I), a cyano group, a $C_1$ to $C_{30}$ linear or branched alkyl group, for example a $C_1$ to $C_{10}$ linear or branched alkyl group, a $C_6$ to $C_{30}$ aryl group, for example a $C_6$ to $C_{12}$ aryl group, a $C_2$ to $C_{30}$ heteroaryl group, for example a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+1}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein each of R and R' are independently hydrogen or a $C_1$ to $C_{10}$ alkyl group), an amidino group (—C(=NH)NH$_2$), a nitro group (—NO$_2$), an amide group (—C(=O)N(H)R, wherein R is hydrogen or a C$_1$ to C$_{10}$ alkyl group), an aldehyde group (—C(=O)H), a hydroxy group (—OH), a sulfonyl group (—S(=O)$_2$R, wherein R is hydrogen or a C$_1$ to C$_{10}$ alkyl group), and a carbamate group (—NHC(=O)OR, wherein R is a C$_1$ to C$_{10}$ alkyl group), instead of hydrogen of the functional group or the compound, provided that the substituted atom's normal valence is not exceeded.

According to some example embodiments, a fused polycyclic heteroaromatic compound is represented by represented by Chemical Formula 1 having a compact planar structure in which seven or more aromatic rings and heteroaromatic rings are fused together.

[Chemical Formula 1]

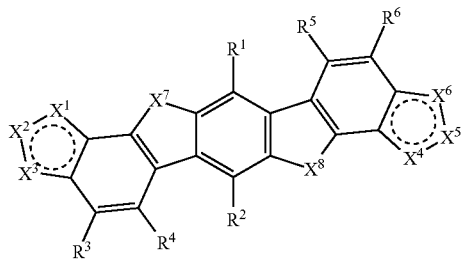

In Chemical Formula 1,

X$^1$ to X$^8$ are independently one of S, Se, Te, N—R$^a$, and C—R$^b$, wherein R$^a$ and R$^b$ are independently one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group, one of X$^1$ to X$^3$ is one of S, Se, Te, and N—R$^a$ and remaining two of X$^1$ to X$^3$ are C—R$^b$ wherein R$^b$ is one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group, or R$^b$'s are linked with each other to provide a C$_5$ aromatic ring or a C$_6$ aromatic ring, one of X$^4$ to X$^6$ is one of S, Se, Te, and N—R$^a$, and remaining two of X$^4$ to X$^6$ are C—R$^b$ wherein R$^b$ is one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group or R$^b$'s are linked with each other to provide a C$_5$ aromatic ring or a C$_6$ aromatic ring, each of R$^3$ to R$^6$ is independently one of hydrogen, a halogen, a cyano group, a C$_1$ to C$_4$ alkyl group, and a C$_1$ to C$_4$ fluoroalkyl group, for example a trifluoroalkyl group, and each of R$^1$ and R$^2$ is independently a functional group represented by Chemical Formula 2,

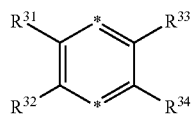

[Chemical Formula 2]

wherein, in Chemical Formula 2,

L is an ethynylene group or a functional group represented by Chemical Formula 2-1, and Y$^1$ is one of hydrogen, a halogen, a cyano group, —Si(R$^x$)(R$^y$)(R$^z$) (wherein each of R$^x$, R$^y$, and R$^z$ are independently one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group), a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group,

[Chemical Formula 2-1]

$$R^{31} \underset{R^{32}}{\overset{*}{\diagup}} \underset{*}{\diagdown} \underset{R^{34}}{\overset{R^{33}}{}}$$

wherein, in Chemical Formula 2-1, each of R$^{31}$ to R$^{34}$ is independently one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group or optionally R$^{31}$ and R$^{32}$ are linked with each other to provide a C$_5$ aromatic ring or a C$_6$ aromatic ring or optionally R$^{33}$ and R$^{34}$ are linked with each other to provide a C$_5$ aromatic ring or a C$_6$ aromatic ring.

The fused polycyclic heteroaromatic compound represented by Chemical Formula 1 has a structure in which seven or more aromatic rings and heteroaromatic rings are fused together. By having a compact planar molecular structure, the fused polycyclic heteroaromatic compound has a uniform and stable oxidation potential when applied to an actual device, and shows high charge mobility since the intermolecular packing and stacking are improved. Thereby, it is easily synthesized to be effectively applied to a semiconductor material, an electron transporting material, or the like.

The fused polycyclic heteroaromatic compound represented by Chemical Formula 1 includes a linking group like L (ethynylene or a functional group represented by Chemical Formula 2-1) at positions of R$^1$ and R$^2$, which provides a rigid bond and suppresses a free rotation of bonds between a benzene ring and L and between L and Y$^1$ and thus improve intermolecular packing and stacking.

In addition, the functional group represented by Chemical Formula 2 is present at the positions of R$^1$ and R$^2$ in a vertical direction with respect to a length direction axis of the fused polycyclic heteroaromatic compound represented by Chemical Formula 1 and thus may improve organic dissolubility for a solvent. Accordingly, the fused polycyclic heteroaromatic compound may be well formed into a thin film having a thin large area as well as simply coated through a room temperature solution process due to this dissolubility improvement and thus effective in terms of processibility and workability. In addition, when formed into a thin film through a deposition, thin film uniformity may be improved by inducing a predetermined intermolecular alignment of the compound.

In addition, the functional group represented by Chemical Formula 2 present at the position of R$^1$ and R$^2$ in a vertical direction with respect to the length direction axis of the fused polycyclic heteroaromatic compound may facilitate the molecular alignment and improve intermolecular packing and stacking during the formation of a thin film.

In addition, the $Y^1$ substituent is present at a para position as shown in Chemical Formula 2-1 and further improves the intermolecular packing and stacking during the formation of a thin film.

The aromatic rings condensed in a length direction so that the functional group represented by Chemical Formula 2 may be present at the positions of $R^1$ and $R^2$ in a vertical direction with respect to the length direction axis of the fused polycyclic heteroaromatic compound are fused to keep linearity.

The fused polycyclic heteroaromatic compound represented by Chemical Formula 1 may be one of compounds represented by Chemical Formulae 1-1 to 1-3.

[Chemical Formula 1-1]

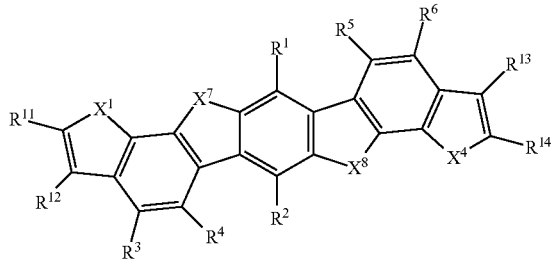

[Chemical Formula 1-2]

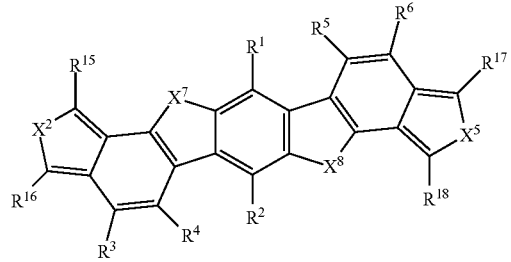

[Chemical Formula 1-3]

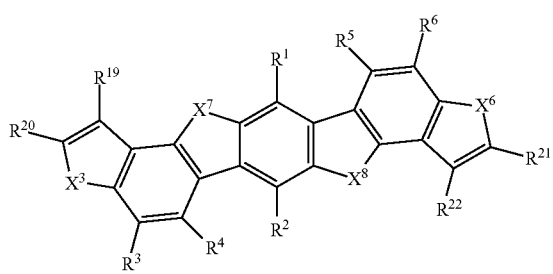

In Chemical Formulae 1-1 to 1-3, $R^1$ to $R^6$ are the same as in Chemical Formula 1, each of $X^1$ to $X^8$ is one of S, Se, Te, and N—$R^a$, wherein $R^a$ is one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, and each of $R^{11}$ to $R^{22}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, or optionally at least one of $R^{11}$ and $R^{12}$ and $R^{13}$ and $R^{14}$ or at least one of $R^{19}$ and $R^{20}$ and $R^{21}$ and $R^{22}$ are linked with each other to provide a $C_5$ aromatic ring or a $C_6$ aromatic ring.

In Chemical Formulae 1-1 to 1-3, $X^1$ and $X^4$, $X^2$ and $X^5$, and $X^3$ and $X^6$ are respectively symmetrical to each other and crystallinity of the compound is improved and intermolecular packing or stacking characteristics are also improved.

For example, the compound represented by Chemical Formula 1-1 may be formed by fusing Chemical Formula 1-1A, 1-1B, and 1-1C.

[Chemical Formula 1-1A]

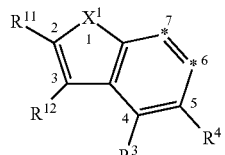

[Chemical Formula 1-1B]

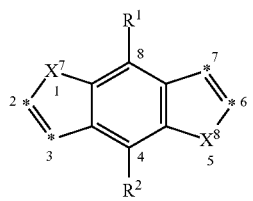

[Chemical Formula 1-1C]

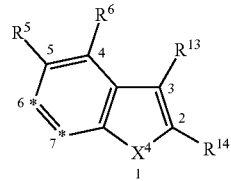

The position Nos. 6 and 7 of Chemical Formula 1-1A are fused with position Nos. 2 and 3 of Chemical Formula 1-1B, and the position Nos. 6 and 7 are fused with position Nos. 6 and 7 of Chemical Formula 1-1C. Herein, the length direction axis of the fused polycyclic heteroaromatic compound may be substantially vertical with respect to an axis of a benzene ring bonded with $R^1$ and $R^2$. Accordingly, a molecular alignment of the compound may be easily obtained and improve intermolecular packing or stacking during the formation of a thin film.

A length direction axis of the fused polycyclic heteroaromatic compounds represented by Chemical Formulae 1-2 and 1-3 like the fused polycyclic heteroaromatic compound represented by Chemical Formula 1-1 may be substantially vertical with respect to an axis of a benzene ring bonded with $R^1$ and $R^2$.

In Chemical Formula 1, one of $X^1$ to $X^3$ may independently be a sulfur atom (S) or a selenium atom (Se) and one of $X^4$ to $X^6$ may independently be a sulfur atom (S) or a selenium atom (Se). When one of $X^1$ to $X^3$ and/or one of $X^4$ to $X^6$ are S or Se, intermolecular packing or stacking may be improved.

In Chemical Formula 1, the $C_5$ aromatic ring or the $C_6$ aromatic ring may respectively be an $X^9$-containing ring and an $X^{10}$-containing ring wherein $X^9$ and $X^{10}$ are independently one of O, S, Se, Te, N—$R^a$, and $C(R^c)$=$C(R^d)$, wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group. Specific examples of the $C_5$ aromatic ring and the $C_6$ aromatic ring may be a thiophene ring, a selenophene ring, a furan ring, a benzene ring, and the like.

In Chemical Formula 1, the $X^9$-containing ring and the $X^{10}$-containing ring expand a conjugation structure and intermolecular interactions may be increased and thereby charge mobility and thermal stability of the compound may be improved.

In Chemical Formula 2, the $C_5$ aromatic ring or the $C_6$ aromatic ring may respectively be an $X^{11}$-containing ring and an $X^{12}$-containing ring, wherein $X^{11}$ and $X^{12}$ are independently one of O, S, Se, Te, N—$R^a$, and $C(R^c)\!=\!C(R^d)$, wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group. Specific examples of the $C_5$ aromatic ring and the $C_6$ aromatic ring may be a thiophene ring, a selenophene ring, a furan ring, a benzene ring, and the like.

The functional group represented by Chemical Formula 2-1 may be one of functional groups represented by Chemical Formula 2-1-1.

[Chemical Formula 2-1-1]

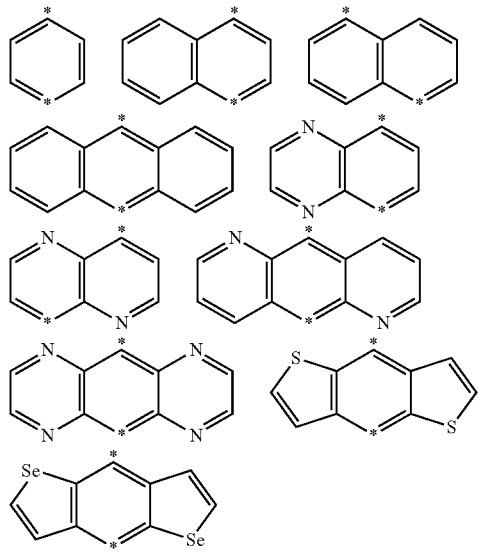

In Chemical Formula 2-1-1, one of *'s indicates a bonding site with Chemical Formula 1 and the other indicates a bonding site with $Y^1$ of Chemical Formula 2.

In Chemical Formula 2-1-1, hydrogen of each aromatic ring may be replaced by a substituent, for example one of a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted C2 to C30 alkylheteroaryl group, a substituted or unsubstituted $C_5$ to $C_{30}$ cycloalkyl group, and a substituted or unsubstituted $C_2$ to $C_{30}$ heterocycloalkyl group.

The fused polycyclic heteroaromatic compound according to some example embodiments may have an average molecular weight of about 300 to about 3000, for example about 300 to about 1000. Within the range of the average molecular weight, it may be easy to handle.

Specific examples of the fused polycyclic heteroaromatic compound may be compounds of Chemical Formula 1-1-1, 1-2-1, or 1-3-1.

[Chemical Formula 1-1-1]

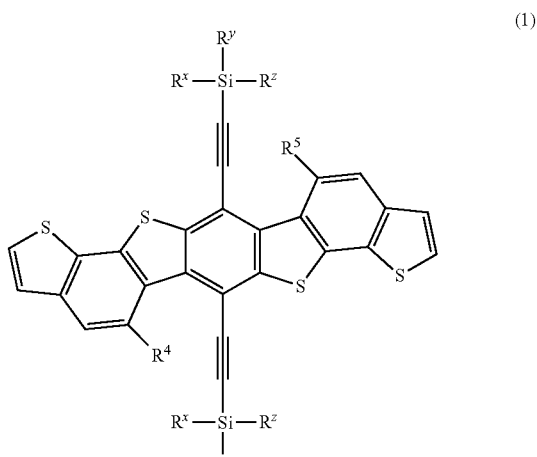

(1)

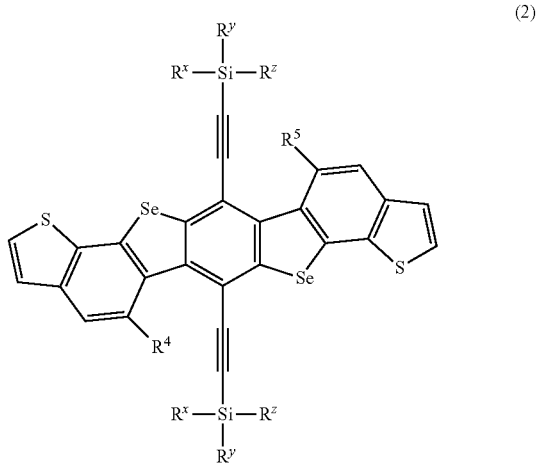

(2)

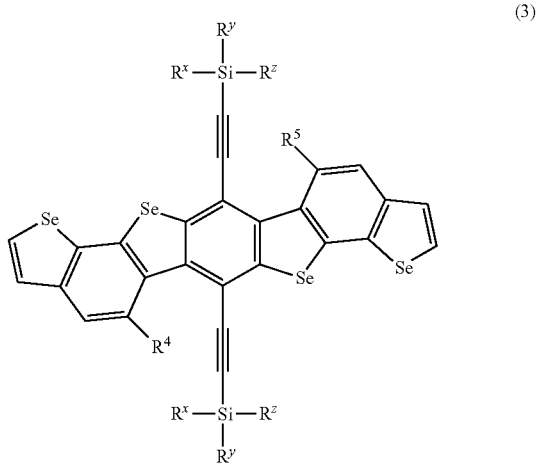

(3)

-continued
(4)
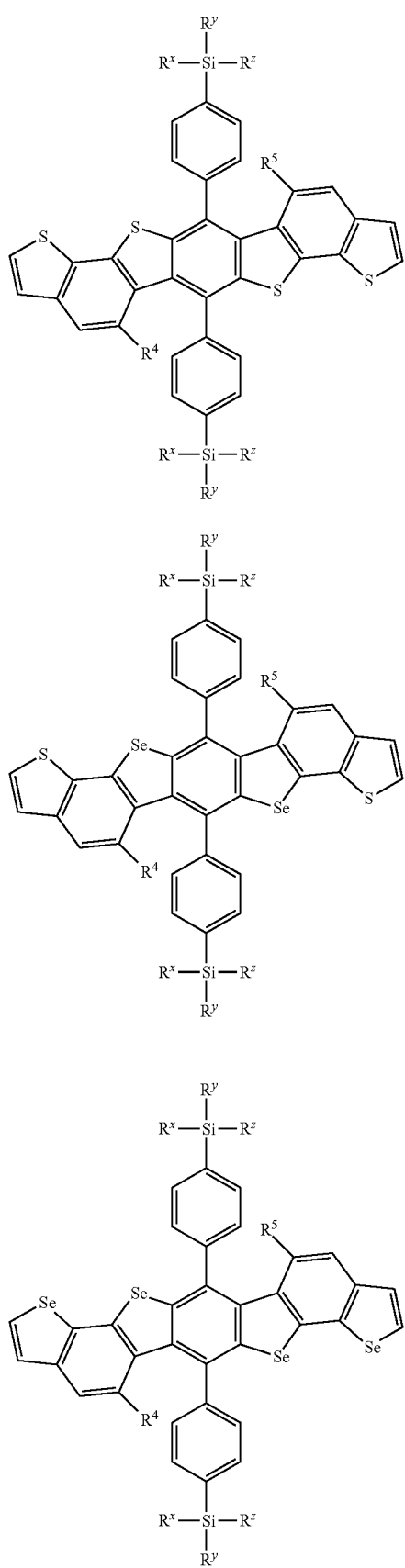
(5)
(6)
[Chemical Formula 1-2-1]
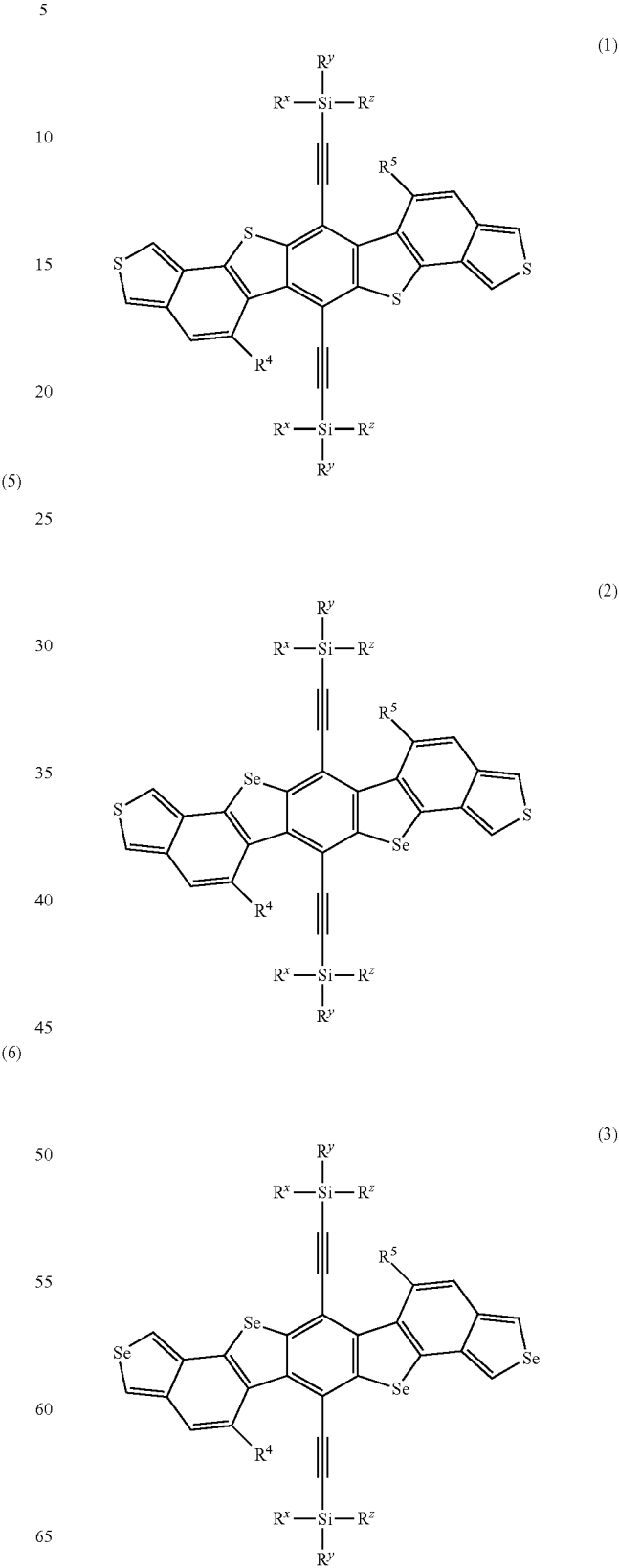
(1)
(2)
(3)

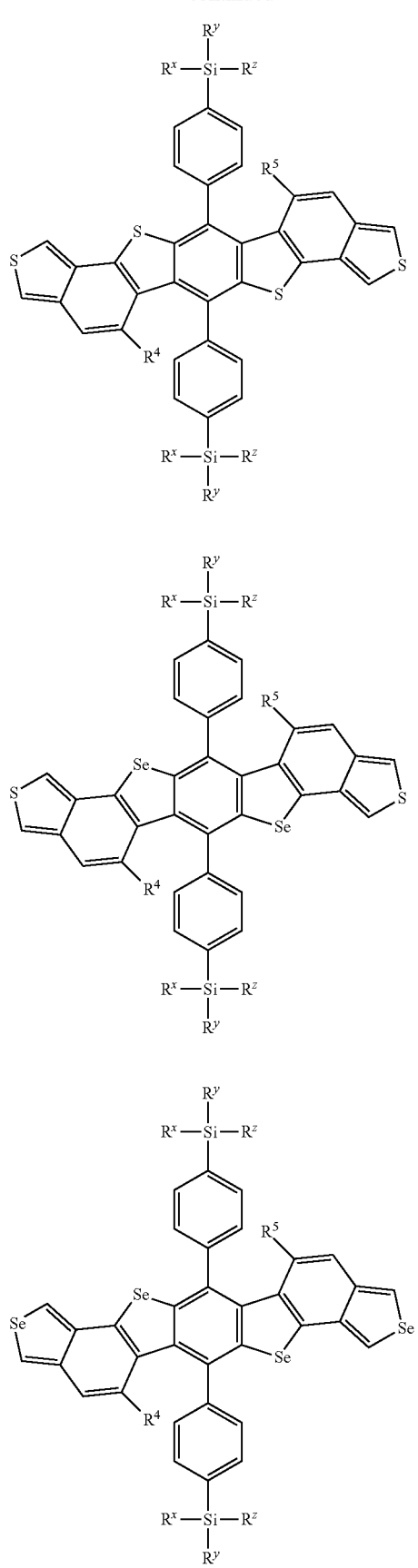
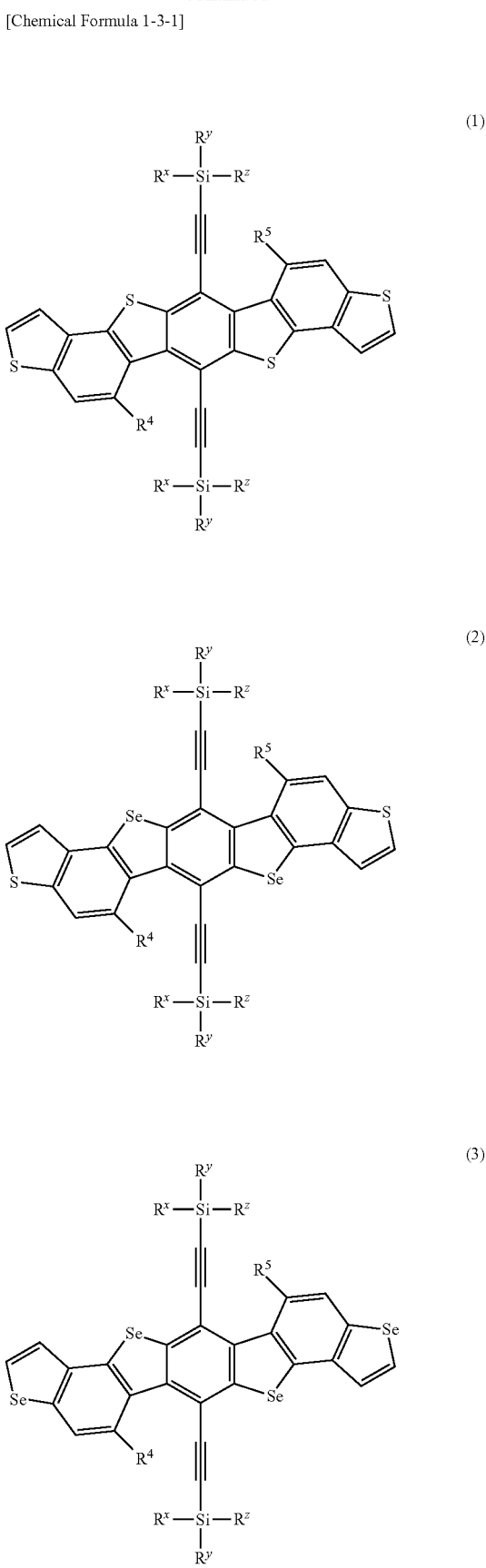
[Chemical Formula 1-3-1]

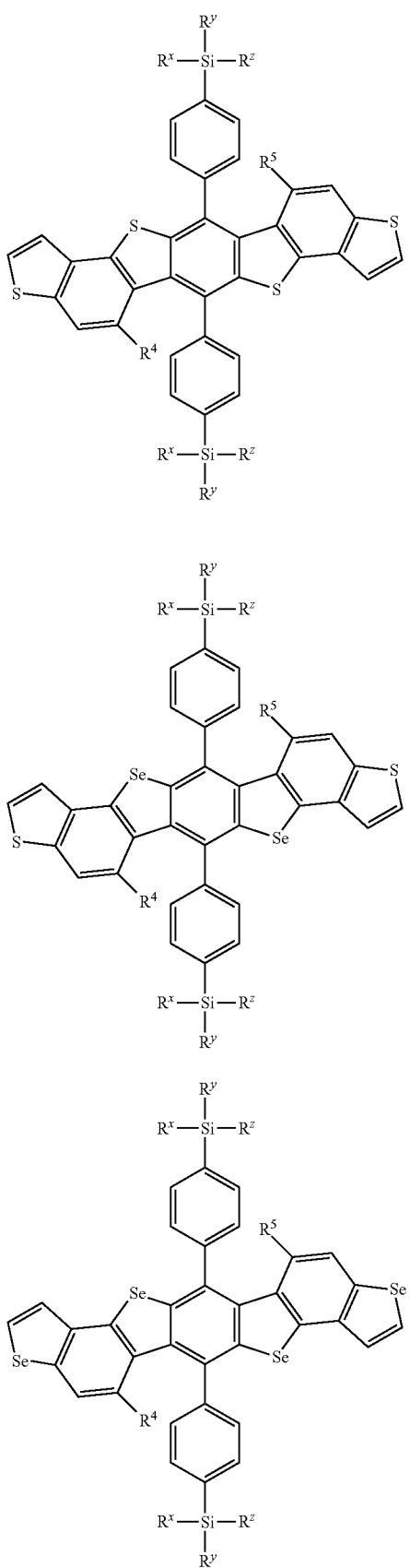

In Chemical Formulae 1-1-1, 1-2-1, and 1-3-1, each of $R^4$ and $R^5$ are independently one of hydrogen, a halogen, a cyano group, a $C_1$ to $C_4$ alkyl group, and a $C_1$ to $C_4$ fluoroalkyl group, for example a trifluoroalkyl group, and each of $R^x$, $R^y$, $R^z$, $R'^x$, $R'^y$, and $R'^z$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, a substituted or unsubstituted $C_4$ to $C_{10}$ heteroaryl group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

In Chemical Formulae 1-1-1, 1-2-1, and 1-3-1, hydrogen of each aromatic ring may be replaced by a substituent, for example one of a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group.

The fused polycyclic heteroaromatic compound may be prepared according to a general method, for example, chemical or electrochemical oxidation synthesis, which is a representative method of polymerizing an aromatic compound or a heteroaromatic compound, or condensation polymerization using a compound of an organic transition element such as nickel or palladium.

The fused polycyclic heteroaromatic compound may be mixed with a polymer. Examples of the polymer may be polystyrene, polyaniline, polythiophene, a diketopyrrolopyrrole (DPP)-based polymer, polyacetylene, polythienylenevinylene, polyphenylene, polyphenylenevinylene, polypyrrole, polyquinoline, or a derivative thereof. In this way, when the low molecular fused polycyclic heteroaromatic compound is mixed with the polymer, a uniform thin film may be formed, and the polymer may play a role of a protective layer for the fused polycyclic heteroaromatic compound and resultantly, improve reliability of a device.

The fused polycyclic heteroaromatic compound and the polymer may be used in a weight ratio of about 10:90 to about 90:10, for example, about 10:90 to about 50:50.

Example embodiments provide an organic thin film including the fused polycyclic heteroaromatic compound and an electronic device including the organic thin film.

The organic thin film according to some example embodiments includes the fused polycyclic heteroaromatic compound, so it may be applied to an organic semiconductor layer for an electronic device, or a carrier transport layer such as a channel layer. The electronic device including the same may have improved electrical properties such as high charge mobility as well as improved processibility and workability.

The organic thin film may be manufactured by depositing the fused polycyclic heteroaromatic compound on a substrate according to the general method, or dissolving the fused polycyclic heteroaromatic compound in an organic solvent and then coating the same at room temperature according to a solution process. If required, heating treatment may be performed after the deposition or coating process to further enhance the densification and uniformity of the thin film.

Particularly, the organic solvent may include at least one kind of general organic solvent, for example, at least one kind of an aliphatic hydrocarbon solvent such as hexane, heptane, or the like; an aromatic hydrocarbon solvent such as toluene, pyridine, quinoline, anisole, mesitylene, xylene, or the like; a ketone-based solvent such as methyl isobutyl ketone, 1-methyl-2-pyrrolidinone, cyclohexanone, acetone, or the like; an ether-based solvent such as tetrahydrofuran, isopropyl ether, or the like; an acetate-based solvent such as ethyl acetate, butyl acetate, propylene glycol methyl ether acetate, or the like; an alcohol-based solvent such as isopropyl alcohol, butanol, or the like; an amide-based solvent such as dimethyl acetamide, dimethyl formamide, or the like; a silicone-based solvent; and a mixture of solvents. The amount of the fused polycyclic heteroaromatic compound dissolved in the organic solvent may be adequately selected and determined by a person of ordinary skill in the art, for example, in a range of about 0.01 wt % to about 50 wt % in the total solvent in view of solubility and coating property.

The method of providing an organic thin film may include a wet process such as screen printing, printing, imprinting, spin casting, dipping, ink jetting, roll coating, flow coating, drop casting, spray coating, roll printing, and the like or a dry process such as thermal evaporation, vacuum deposition, laser deposition, and the like. The heat treatment may be performed at about 80 to about 250° C. for about 1 minute to about 2 hours, but is not limited thereto.

A thickness of the organic thin film may be adjusted according to the usage and the case considering the kinds of the used compound and solvent by a person of ordinary skill in the art, and is specifically in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory device, and/or a sensor, and the organic thin film may be applied to each device according to the general process commonly known in the art.

For example, the transistor includes: a gate electrode disposed on a substrate; a source electrode and a drain electrode facing each other and defining a channel region; an insulation layer electrically insulating the source electrode and drain electrode and the gate electrode; and an active layer including the fused polycyclic heteroaromatic compound formed in the channel region.

The active layer may be obtained by depositing the fused polycyclic heteroaromatic compound or a mixture of the fused polycyclic heteroaromatic compound and the polymer or coating a composition including the fused polycyclic heteroaromatic compound or the fused polycyclic heteroaromatic compound and the polymer by a solution process, e.g., a screen printing method, a printing method, a spin coating method, a dipping method, an inkjet method, etc. A solvent for preparing the composition may be toluene, chloroform, dichloromethane, tetrahydrofuran, chlorobenzene, dichlorobenzene, tetralin, xylene, etc. When the active layer is formed by the solution process, the process cost may be reduced, and a relatively wide area device may be effectively manufactured.

Figure 2:
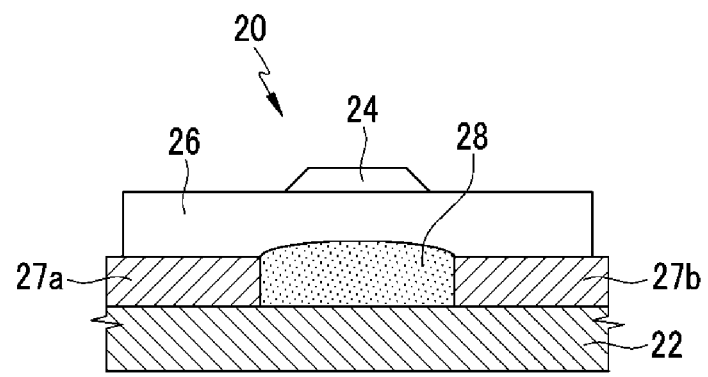
FIG. 2 is a schematic cross-sectional view of a transistor according to some example embodiments.

FIGS. 1 and 2 are schematic cross-sectional views showing transistors according to some example embodiments. The transistor according to some example embodiments may be a thin film transistor. The thin film transistor may be a thin film having a thickness of several nanometers to several microns.

Referring to FIG. 1, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the fused polycyclic heteroaromatic compound.

Referring to FIG. 2, a transistor 20 includes a source electrode 27a and a drain electrode 27b defining a channel region and that are formed on a substrate 22, and an active layer 28 formed on the channel region. The active layer 28 includes the fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES), and the inorganic material may include, for example, glass or a metal.

In addition, the gate electrodes 14 and 24, source electrodes 17a and 27a, and drain electrodes 17b and 27b may include a generally-used metal, for example, gold (Au), silver (Ag), aluminum (Al), nickel (Ni), or indium tin oxide (ITO), but the metal is not limited thereto.

The insulation layers 16 and 26 may include a generally-used insulator having a high dielectric constant, for example, a ferroelectric insulator, e.g., $Ba_{0.33}Sr_{0.66}TiO_3$ (BST, barium strontium titanate), $Al_2O_3$, $Ta_2O_5$, $La_2O_5$, $Y_2O_3$, and $TiO_2$; an inorganic insulator, e.g., $PbZr_{O.33}Ti_{O.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_x$ (x is determined depending on the valence of Si), (aluminum oxynitride), etc.; or an organic insulator, e.g., polyimide, BCB (benzocyclobutane), parylene, polyacrylate, polyvinyl alcohol, polyvinylphenol, etc., but it is not limited thereto.

Figure 3:
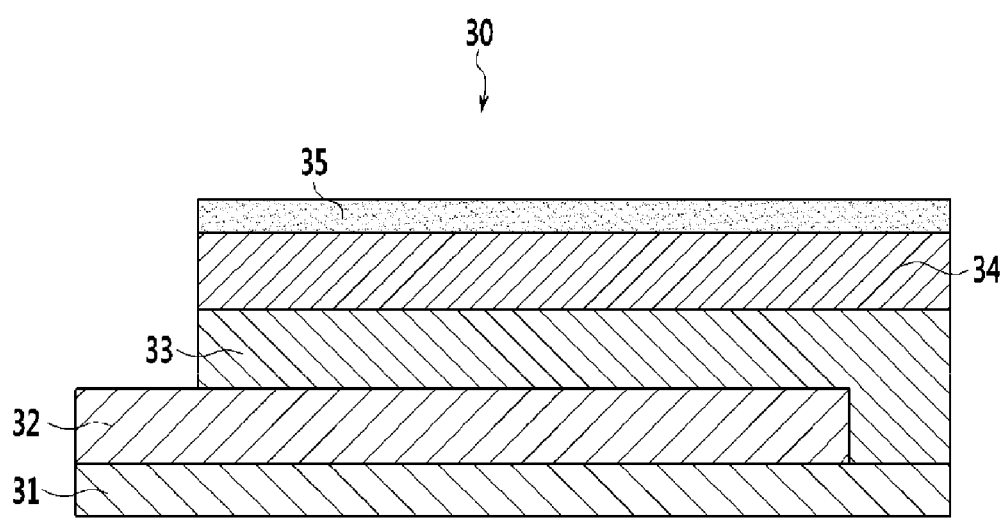
FIG. 3 is a schematic cross-sectional view showing a solar cell according to some example embodiments.

Hereinafter, a solar cell according to some example embodiments is illustrated referring to FIG. 3. FIG. 3 provides a schematic cross-sectional view showing a solar cell according to some example embodiments.

Referring to FIG. 3, the solar cell 30 includes an anode 32 on a substrate 31.

The substrate 31 may be made of any transparent material allowing an external light to be entered without any particular limit. Accordingly, the transparent substrate 31 may be made of glass or plastics. Examples of the plastic may include polyethyleneterephthalate (PET), polyethylene naphthalate (PEN), polycarbonate (PC), polypropylene (PP), polyimide (PI), triacetyl cellulose (TAC), a copolymer thereof, or the like.

The anode 32 may be made of a material with high work function for hole injection for example, a transparent oxide such as indium tin oxide (ITO), fluorine tin oxide (FTO), indium oxide, and the like.

On the anode 32, a hole transport layer (HTL) 33 may be disposed. The hole transport layer (HTL) 33 may include a conductive polymer such as poly(3,4-ethylenedioxy-thiophene) (PEDOT) doped with poly(styrenesulfonate) (PSS) (PEDOT:PSS), polyaniline doped with poly(styrenesulfonic acid) (PAni:PSS), polypyrrole, poly(p-phenylenevinylene), poly[2-methoxy-5-(2'-ethyl-hexyloxy)-1,4-phenylene vinylene] (MEH-PPV), poly[2-methoxy-5-(3,7-dimethyloctyloxy)-1,4-phenylene-vinylene) (MDMO-PPV), poly(3-alkylthiophene), polythiophene, and the like; pentacene; CuPc; or a triphenyldiamine derivative (TPD).

On the hole transport layer (HTL) 33, a photoactive layer 34 may be disposed. The photoactive layer may include an electron donor (p-type semiconductor) material and an electron accepter (n-type semiconductor) material. The electron donor may include the fused polycyclic heteroaromatic compound. The electron acceptor may include fullerene with large electron affinity (C60, C70, C74, C76, C78, C82, C84, C720, C860); a fullerene derivative such as 1-(3-methoxy-carbonyl)propyl-1-phenyl(6,6)C61 (PCBM); or a mixture thereof.

On the photoactive layer 34, a cathode 35 is disposed. The cathode 35 may be made of an alkali metal such as lithium (Li), sodium (Na), and the like; an alkali-earth metal such as beryllium (Be), magnesium (Mg), and the like; aluminum (Al); transition elements such as silver (Ag), gold (Au), cobalt (Co), iridium (Ir), nickel (Ni), osmium (Os), palladium (Pd), platinum (Pt), and the like; a rare earth element; a semi-metal such as selenium (Se), and the like; a metal alloy such as a sodium-potassium alloy, a magnesium-indium alloy, an aluminum-lithium alloy, and the like; LiF/Al, and the like. Although not shown in the drawing, an electron transport layer (ETL) may be further formed between the photoactive layer 34 and cathode 35.

On the other hand, a photocurrent is generated when a light is absorbed in the photoactive layer 34 and excites a pair of electron-hole, the excited pair of electron-hole are diffused and reach an interface of an electron-acceptor and an electron-donor and then, separated into electrons and holes due to electron affinity difference of two materials at the interface, the electrons move through the electron acceptor to a cathode 35 while the hole move through the electron-donor to an anode 32.

Hereinafter, the example embodiments are illustrated in more detail with reference to some example embodiments. These examples, however, are not in any sense to be interpreted as limiting the scope of the example embodiments.

Examples

Example 1: Synthesis of Fused Polycyclic Heteroaromatic Compound

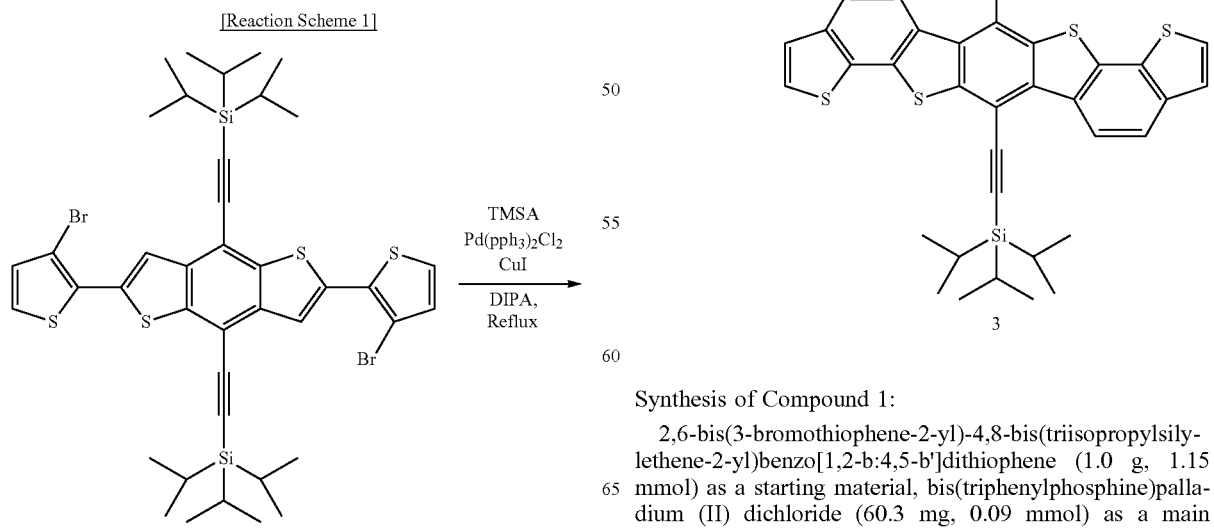

Synthesis of Compound 1:

2,6-bis(3-bromothiophene-2-yl)-4,8-bis(triisopropylsilylethene-2-yl)benzo[1,2-b:4,5-b']dithiophene (1.0 g, 1.15 mmol) as a starting material, bis(triphenylphosphine)palladium (II) dichloride (60.3 mg, 0.09 mmol) as a main catalyst, and copper iodide (CuI; 32.7 mg, 0.17 mmol) as an assistant catalyst are dissolved in 150 mL of dry diisopropylamine. The obtained solution is nitrogen-bubbled for 30 minutes. Subsequently, ethynyl trimethylsilane (3.3 mL, 23.0 mmol) is added thereto in a dropwise fashion and then, refluxed and stirred for 3 days by increasing its temperature. Then, an ammonium chloride-saturated solution (150 mL) is added thereto, and an organic layer is extracted therefrom by using chloroform and water, dried with MgSO4, and concentrated under a reduced pressure. Subsequently, a product therefrom is purified through silica chromatography to obtain a yellow solid, Compound 1. (Yield=74%)

$^1$H NMR (300 MHz, CDCl$_3$): δ ppm 7.81 (s, 1H), 7.21 (d, 1H), 7.11 (d, 1H), 1.23 (m, 21H), 0.30 (s, 9H)

Synthesis of Compound 2:

Compound 1 (0.99 g, 1.09 mmol) is dissolved in 70 mL of dry tetrahydrofuran and 35 mL of dry methyl alcohol. Subsequently, potassium hydroxide (61 mg, 1.09 mmol) is added thereto. The obtained mixture is stirred at room temperature for 10 minutes. 100 mL of an ammonium chloride-saturated solution is added thereto, and an organic layer is extracted therefrom by using chloroform and water, dried with MgSO$_4$, and concentrated under a reduced pressure. Subsequently, a product therefrom is purified through silica chromatography to obtain a yellow solid, Compound 2. (Yield=73%)

$^1$H NMR (300 MHz, CDCl$_3$): δ ppm 8.07 (s, 1H), 7.24 (d, 1H), 7.15 (d, 1H), 3.40 (s, 1H), 1.24 (m, 21H)

$^{13}$C NMR (500 MHz, CDCl$_3$): δ ppm 141.05, 140.07, 138.96, 137.45, 132.50, 124.89, 121.24, 118.32, 111.67, 102.53, 102.45, 83.33, 79.12, 19.04, 11.55.

Synthesis of Compound 3:

Compound 2 (0.34 g, 0.45 mmol) is dissolved in 30 mL of dry toluene. The obtained solution is nitrogen-bubbled for 30 minutes. Subsequently, platinum chloride (PtCl$_2$; 30 mg, 11 mmol) is added thereto, and the mixture is heated up to 115° C. and stirred for 3 days. An organic layer formed therein is passed through a filter filled with celite under a reduced pressure and concentrated under the reduced pressure. Subsequently, the organic layer is purified through silica chromatography to obtain an orange solid, Compound 3. (Yield=10%)

$^1$H NMR (300 MHz, CDCl$_3$): δ ppm 9.38 (d, 1H), 7.91 (d, 1H), 7.56 (d, 1H), 7.52 (d, 1H), 1.35 (m, 21H)

$^{13}$C NMR (500 MHz, CDCl$_3$): δ ppm 143.08, 139.33, 134.39, 133.43, 133.18, 132.46, 126.50, 125.03, 121.35, 120.37, 112.65, 106.49, 103.28, 19.08, 11.75

Example 2: Manufacture of Organic Thin Film Transistor (OTFT)

First, chromium used as a gate electrode is deposited to be 1000 Å thick through sputtering on a cleaned glass substrate, and SiO$_2$ is deposited to form a 3000 Å-thick insulation layer thereon in a CVD method. Then, Au is deposited thereon to be 700 Å thick through sputtering, forming a source electrode and a drain electrode. The glass substrate is washed with isopropyl alcohol for 10 minutes and dried before coating an organic semiconductor material. In addition, the SiO$_2$ used as an insulation layer is treated with UV/O$_3$ for 30 minutes before surface modification.

Then, an OTFT device 10 shown in FIG. 1 is manufactured by dipping a glass structure with electrodes in an octyltrichlorosilane solution diluted in n-hexane into a concentration of 10 mM for 30 minutes, washing it with hexane and alcohol, drying it, and then coating the compound synthesized according to Example 1 dissolved in toluene to form an active layer 18 on the glass structure.

While the example embodiments have been described in connection with what is presently considered to be practical example embodiments, it is to be understood that the example embodiments are not limited to the disclosed embodiments, but, on the contrary, are intended to cover various modifications and equivalent arrangements included within the spirit and scope of the appended claims.

DESCRIPTION OF SYMBOLS

| | |
|---|---|
| 10, 20: | transistor |
| 12, 22: | substrate |
| 16, 26: | insulation layer |
| 18, 28: | active layer |
| 14, 24: | gate electrode |
| 17a, 27a: | source electrode |
| 17b, 27b: | drain electrode |

What is claimed is:

1. A fused polycyclic heteroaromatic compound represented by Chemical Formula 1:

[Chemical Formula 1]

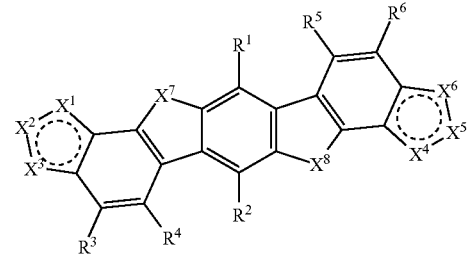

wherein, in Chemical Formula 1,
each of X$^1$ to X$^8$ is independently one of S, Se, Te, N—R$^a$, and C—R$^b$, wherein R$^a$ and R$^b$ are independently one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group,
one of X$^1$ to X$^3$ is one of S, Se, Te, and N—R$^a$ and remaining two of X$^1$ to X$^3$ are C—R$^b$ wherein R$^b$ is one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group or R$^b$'s are linked with each other to provide a C$_5$ aromatic ring or a C$_6$ aromatic ring,
one of X$^4$ to X$^6$ is one of S, Se, Te, and N—R$^a$ and remaining two of X$^4$ to X$^6$ are C—R$^b$ wherein R$^b$ is one of hydrogen, a halogen, a cyano group, a linear or branched substituted or unsubstituted C$_1$ to C$_{10}$ alkyl group, a substituted or unsubstituted C$_3$ to C$_{10}$ cycloalkyl group, a substituted or unsubstituted C$_6$ to C$_{10}$ aryl group, and a substituted or unsubstituted C$_4$ to C$_{10}$ heteroaryl group or R$^b$'s are linked with each other to provide a C$_5$ aromatic ring or a C$_6$ aromatic ring,
each of R$^3$ to R$^6$ is independently one of hydrogen, a halogen, a cyano group, a C$_1$ to C$_4$ alkyl group, and a C$_1$ to C$_4$ fluoroalkyl group, and each of $R^1$ and $R^2$ is independently a functional group represented by Chemical Formula 2,

*-L-Y$^1$  [Chemical Formula 2]

wherein, in Chemical Formula 2,

L is an ethynylene group or a functional group represented by Chemical Formula 2-1, and $Y^1$ is one of hydrogen, a halogen, a cyano group, —Si($R^x$)($R^y$)($R^z$) (wherein each of $R^x$, $R^y$, and $R^z$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group), a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group,

[Chemical Formula 2-1]

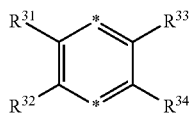

wherein, in Chemical Formula 2-1, each of $R^{31}$ to $R^{34}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group or optionally $R^{31}$ and $R^{32}$ are linked with each other to provide a $C_5$ aromatic ring or a $C_6$ aromatic ring or optionally $R^{33}$ and $R^{34}$ are linked with each other to provide a $C_5$ aromatic ring or a $C_6$ aromatic ring.

2. The fused polycyclic heteroaromatic compound of claim 1, wherein the fused polycyclic heteroaromatic compound represented by Chemical Formula 1 is one of compounds represented by Chemical Formulae 1-1 to 1-3:

[Chemical Formula 1-1]

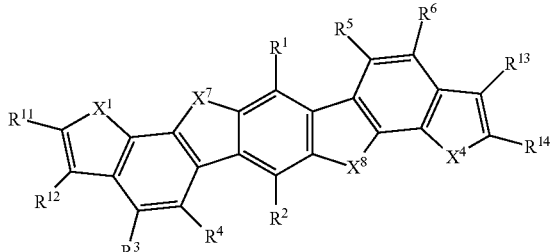

[Chemical Formula 1-2]

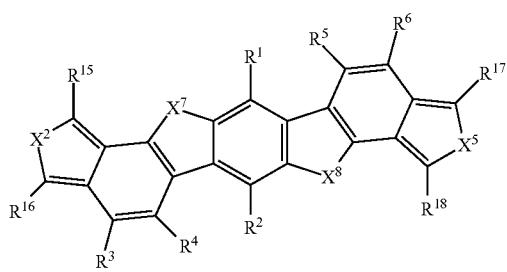

[Chemical Formula 1-3]

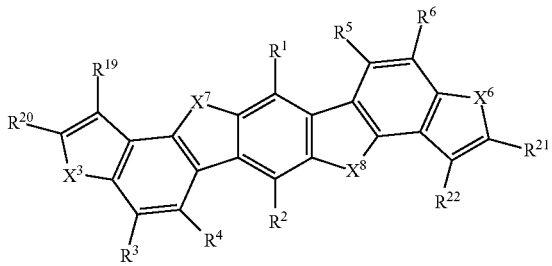

wherein, in Chemical Formulae 1-1 to 1-3, $R^1$ to $R^6$ are same as in Chemical Formula 1, each of $X^1$ to $X^8$ is one of S, Se, Te, and N—$R^a$, wherein $R^a$ is one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, and each of $R^{11}$ to $R^{22}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group, or optionally at least one of $R^{11}$ and $R^{12}$ and $R^{13}$ and $R^{14}$ or at least one of $R^{19}$ and $R^{20}$ and $R^{21}$ and $R^{22}$ are linked with each other to provide a $C_5$ aromatic ring or a $C_6$ aromatic ring.

3. The fused polycyclic heteroaromatic compound of claim 1, wherein in Chemical Formula 1:

one of $X^1$ to $X^3$ is independently a sulfur atom (S) or a selenium atom (Se), and one of $X^4$ to $X^6$ is independently a sulfur atom (S) or a selenium atom (Se).

4. The fused polycyclic heteroaromatic compound of claim 1, wherein in Chemical Formula 1:

the $C_5$ aromatic ring or the $C_6$ aromatic ring is respectively an $X^9$-containing ring and an $X^{10}$-containing ring wherein $X^9$ and $X^{10}$ are independently one of O, S, Se, Te, N—$R^a$, and C($R^c$)=C($R^d$), wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

5. The fused polycyclic heteroaromatic compound of claim 1, wherein in Chemical Formula 2:

the $C_5$ aromatic ring or the $C_6$ aromatic ring is respectively an $X^{11}$-containing ring and an $X^{12}$-containing ring, wherein $X^{11}$ and $X^{12}$ are independently one of O, S, Se, Te, N—$R^a$, and C($R^c$)=C($R^d$), wherein each of $R^a$, $R^c$, and $R^d$ are independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

6. The fused polycyclic heteroaromatic compound of claim 1, wherein the functional group represented by Chemical Formula 2-1 is one of functional groups represented by Chemical Formula 2-1-1:

[Chemical Formula 2-1-1]
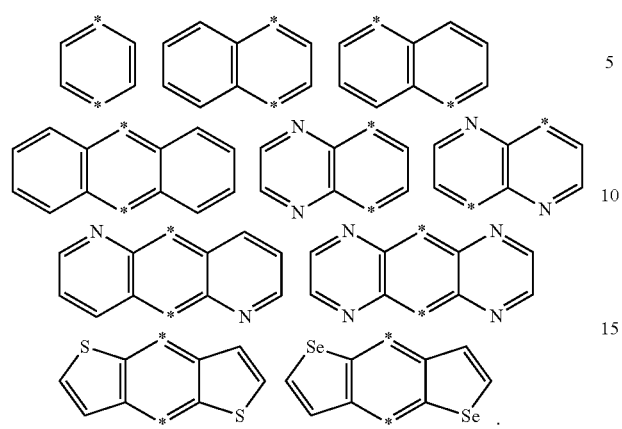
7. The fused polycyclic heteroaromatic compound of claim 1, wherein the fused polycyclic heteroaromatic compound has an average molecular weight of about 300 to about 3000.
8. The fused polycyclic heteroaromatic compound of claim 1, wherein the fused polycyclic heteroaromatic compound is one of compounds of Chemical Formula 1-1-1:
[Chemical Formula 1-1-1]
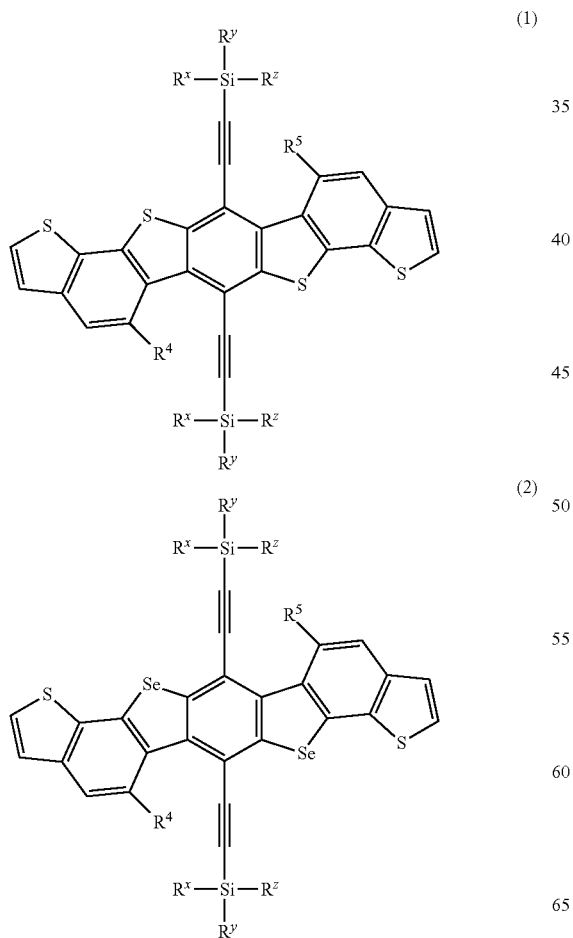
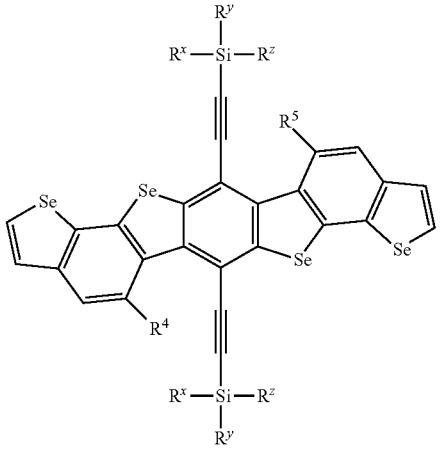
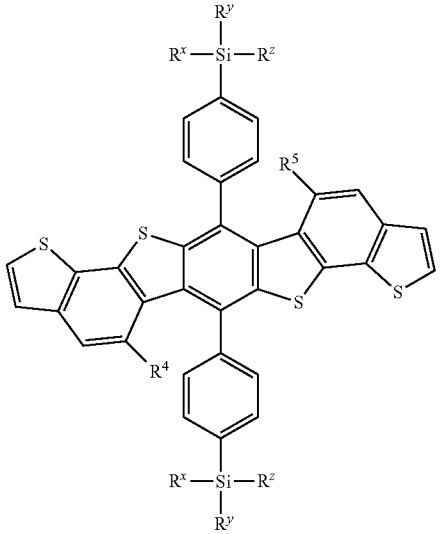
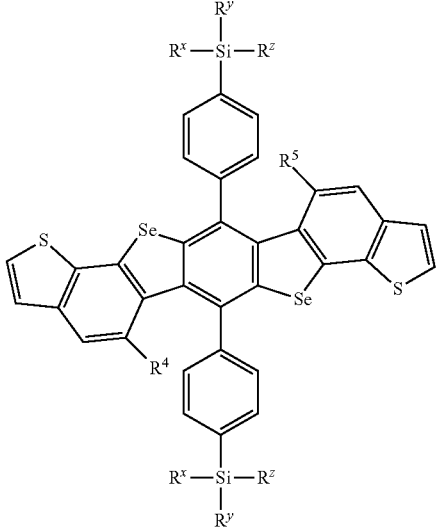

-continued (6)

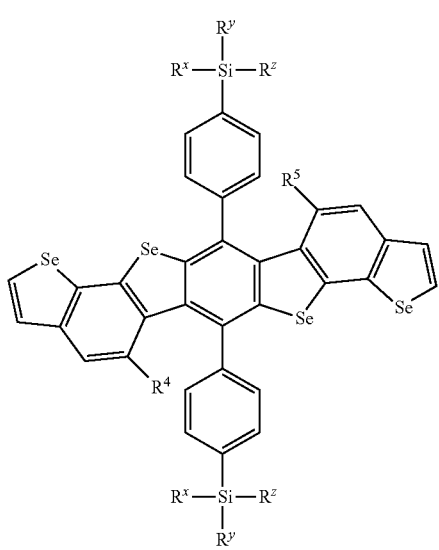

wherein, in Chemical Formula 1-1-1,
each of $R^4$ and $R^5$ is independently one of hydrogen, a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted $C_7$ to $C_{30}$ arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, and
each of $R^x$, $R^y$, $R^z$, $R^{\prime x}$, $R^{\prime y}$, and $R^{\prime z}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, a substituted or unsubstituted $C_4$ to $C_{10}$ heteroaryl group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

9. The fused polycyclic heteroaromatic compound of claim 1, wherein the fused polycyclic heteroaromatic compound is one of compounds of Chemical Formula 1-2-1:

[Chemical Formula 1-2-1]

(1)

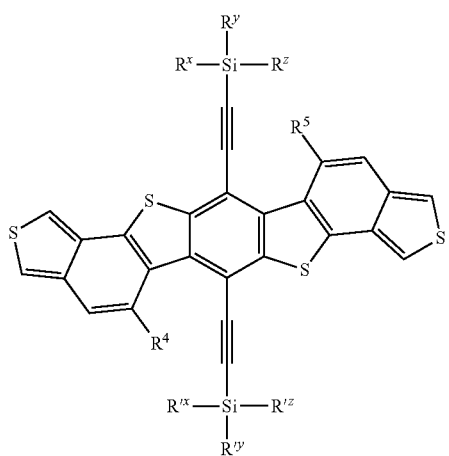

-continued (2)

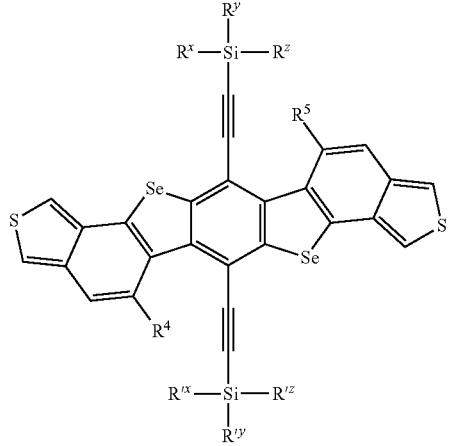

(3)

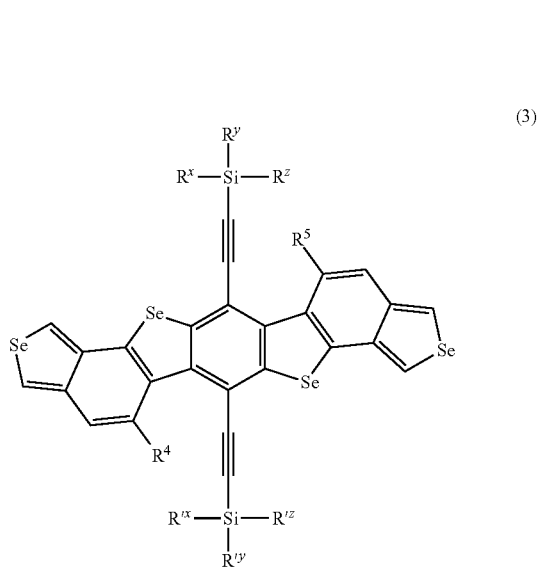

(4)

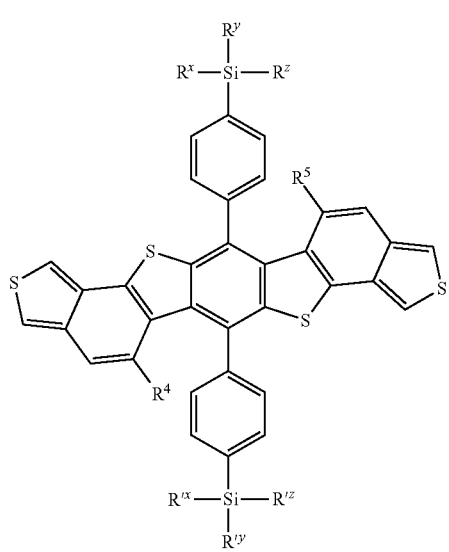

-continued

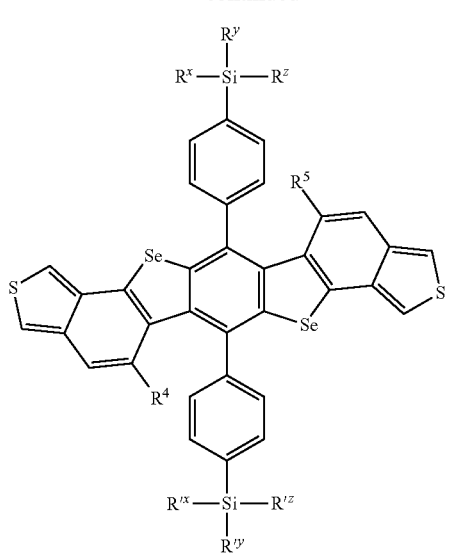
(5)

(6)

wherein, in Chemical Formula 1-2-1,
each of $R^4$ and $R^5$ is independently one of hydrogen, a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted C7 to C30 arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, and each of $R^x$, $R^y$, $R^z$, $R^{\prime x}$, $R^{\prime y}$, and $R^{\prime z}$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, a substituted or unsubstituted $C_4$ to $C_{10}$ heteroaryl group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

10. The fused polycyclic heteroaromatic compound of claim 1, wherein the fused polycyclic heteroaromatic compound is one of compounds of Chemical Formula 1-3-1:

[Chemical Formula 1-3-1]

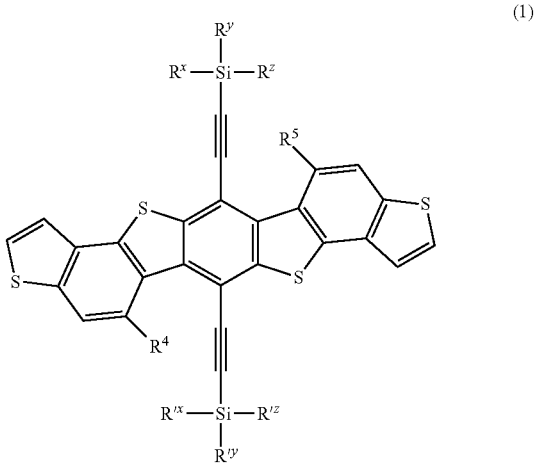
(1)

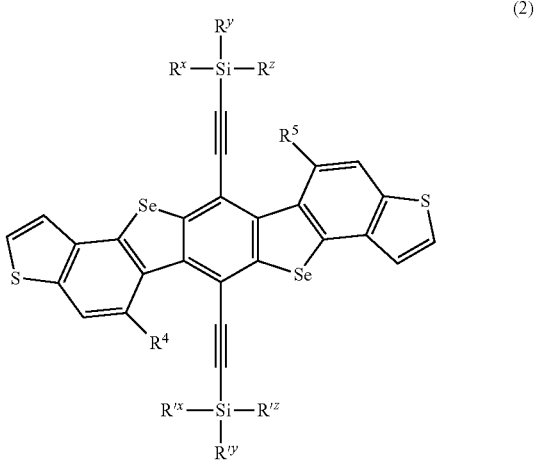
(2)

-continued (3)

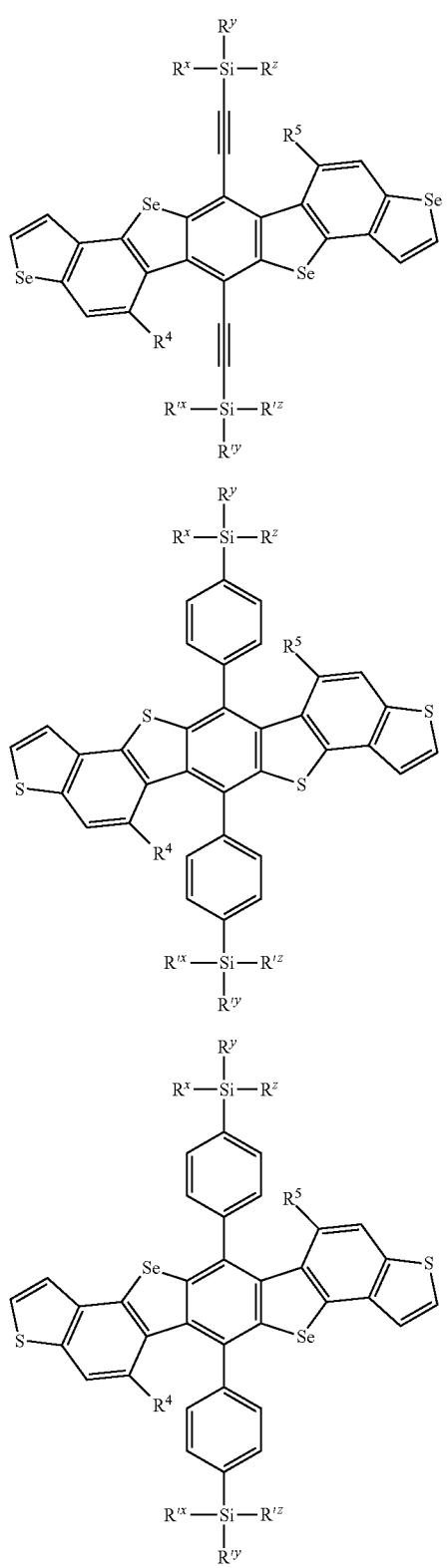

(4)

(5)

-continued (6)

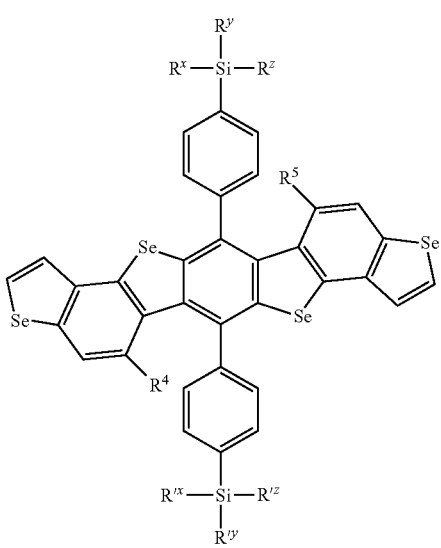

wherein, in Chemical Formula 1-3-1, each of $R^4$ and $R^5$ is independently one of hydrogen, a halogen, a cyano group, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, a substituted or unsubstituted C7 to C30 arylalkyl group, a substituted or unsubstituted $C_2$ to $C_{30}$ heteroarylalkyl group, a substituted or unsubstituted $C_2$ to $C_{30}$ alkylheteroaryl group, a substituted or unsubstituted $C_5$ to $C_{30}$ cycloalkyl group, and a substituted or unsubstituted $C_2$ to $C_{30}$ heterocycloalkyl group, and each of $R^x$, $R^y$, $R^z$, $R'^x$, $R'^y$, and $R'^z$ is independently one of hydrogen, a halogen, a cyano group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, a substituted or unsubstituted $C_4$ to $C_{10}$ heteroaryl group, a linear or branched substituted or unsubstituted $C_1$ to $C_{10}$ alkyl group, a substituted or unsubstituted $C_3$ to $C_{10}$ cycloalkyl group, a substituted or unsubstituted $C_6$ to $C_{10}$ aryl group, and a substituted or unsubstituted $C_4$ to $C_{10}$ heteroaryl group.

11. An organic thin film comprising the fused polycyclic heteroaromatic compound of claim 1.

12. An electronic device comprising the fused polycyclic heteroaromatic compound of claim 1.

13. The electronic device of claim 12, wherein the electronic device is one of a transistor, an organic light emitting diode (OLED), a photovoltaic device, a solar cell, a laser device, a memory device, and a sensor.

* * * * *